United States Patent
Cazer et al.

(10) Patent No.: US 6,562,974 B2
(45) Date of Patent: May 13, 2003

(54) PROCESS FOR MAKING GEMINAL BISPHOSPHONATES

(75) Inventors: Frederick Dana Cazer, Earlville, NY (US); William Douglas Cramer, Cincinnati, OH (US); Dennis Michael Billings, Norwich, NY (US); Gregory Eugene Parry, Lawrenceville, NJ (US)

(73) Assignee: The Procter & Gamble Company, Cincinnati, OH (US)

( * ) Notice: Subject to any disclaimer, the term of this patent is extended or adjusted under 35 U.S.C. 154(b) by 15 days.

(21) Appl. No.: 09/771,899

(22) Filed: Jan. 29, 2001

(65) Prior Publication Data

US 2001/0041690 A1 Nov. 15, 2001

Related U.S. Application Data

(60) Provisional application No. 60/179,506, filed on Feb. 1, 2000.

(51) Int. Cl.$^7$ .................................................. C07F 9/58
(52) U.S. Cl. .......................................... 546/25; 562/13
(58) Field of Search ............................... 562/13; 546/22

(56) References Cited

U.S. PATENT DOCUMENTS

| | | | |
|---|---|---|---|
| 4,054,598 A | 10/1977 | Blum et al. | |
| 4,267,108 A | 5/1981 | Blum et al. | |
| 4,304,734 A | 12/1981 | Jary et al. | |
| 4,327,039 A | 4/1982 | Blum et al. | |
| 4,330,537 A | 5/1982 | Francis | |
| 4,407,761 A | 10/1983 | Blum et al. | |
| 4,447,256 A | 5/1984 | Suzuki et al. | |
| 4,621,077 A | 11/1986 | Rosini et al. | |
| 4,705,651 A | 11/1987 | Staibano | |
| 4,719,203 A | 1/1988 | Bosies et al. | |
| 4,777,163 A | 10/1988 | Bosies et al. | |
| 4,812,316 A | 3/1989 | Rossi et al. | |
| 4,927,814 A | 5/1990 | Gall et al. | |
| 4,939,130 A | 7/1990 | Jaeggi et al. | |
| 4,942,157 A | 7/1990 | Gall et al. | |
| 5,002,937 A | 3/1991 | Bosies et al. | |
| 5,035,898 A | 7/1991 | Chang et al. | |
| 5,039,819 A | 8/1991 | Kieczykowski | |
| 5,049,663 A | 9/1991 | Terada et al. | |
| 5,068,440 A | 11/1991 | Jeffery et al. | |
| 5,091,525 A | 2/1992 | Brennan | |
| 5,110,807 A | 5/1992 | Jaeggi | |
| 5,206,253 A | 4/1993 | Bosies et al. | |
| 5,312,925 A | 5/1994 | Allen et al. | |
| 5,317,015 A | 5/1994 | Ullrich et al. | |
| 5,354,760 A | 10/1994 | Petersen et al. | |
| 5,405,994 A | 4/1995 | Bonnery et al. | |
| 5,480,875 A | 1/1996 | Isomura et al. | |
| 5,525,354 A | 6/1996 | Posti et al. | |
| 5,545,737 A | 8/1996 | Sato et al. | |
| 5,580,977 A | 12/1996 | Henning et al. | |
| 5,583,122 A | 12/1996 | Benedict et al. | |
| 5,602,115 A | 2/1997 | Nugent | |
| 5,760,009 A | 6/1998 | Allen et al. | |

FOREIGN PATENT DOCUMENTS

| | | |
|---|---|---|
| BE | 1000075 A | 2/1988 |
| DE | 2658961 A | 6/1978 |
| EP | 0082472 B1 | 7/1986 |
| EP | 350002 A | 1/1990 |
| EP | 0494844 A1 | 7/1992 |
| EP | 494844 A | 7/1992 |
| EP | 252505 A | 1/1998 |
| GB | 2316945 A | 3/1998 |
| HU | 206726 B | 2/1989 |
| JP | 5598193 C | 7/1980 |
| WO | WO 95/06052 A1 | 3/1995 |
| WO | WO 96/33199 A1 | 10/1996 |
| WO | WO 98 34940 A | 8/1998 |

OTHER PUBLICATIONS

Nicholson et al., "A General Method of Preparation of Tetramethyl Alkyl–1–hydroxy–1,1–diphosphonates", *J. Of Organic Chem.*, vol. 36, pp 3843–3845, 1971.

Ebetino et al., "Elucidation of a Pharmacophore for the Bisphosphonate Mechanism of Bone Antiresorptive Activity", *Phosphorus, Sulfur, and Silicon*, vols. 109–110, pp. 217–220, 1996.

Ebetino et al., "Recent Work on the Synthesis of Phosphonate–Containing, Bone–Active Heterocycles", *Heterocycles*, vol. 30, No. 2, pp. 855–862, 1990.

*Primary Examiner*—Robert Gerstl
(74) *Attorney, Agent, or Firm*—Richard S. Echler, Sr.; Mary Pat McMahon; David V. Upite

(57) ABSTRACT

The present invention relates to a novel process for making geminal bisphosphonates. The process provides for bisphosphorylation using phosphorus trihalide, phosphorous acid as a reactant/solvent, and a base as an acid acceptor/solvent. The present invention is directed to a process for making geminal bisphosphonates of the general formula:

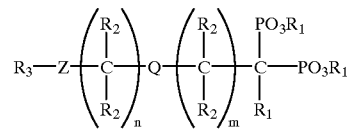

wherein Q is oxygen, —NR4—, sulfur, selenium, or a single bond; m+n is an integer from 0 to about 5, Z is a ring selected from the group consisting of pyridine, pyridazine, pyrimidine, and pyrazine; $R_1$ is hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl; each $R_2$ is independently, hydrogen, or substituted or unsubstituted alkyl (saturated or unsaturated) having from 1 to about 4 carbon atoms; $R_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; $R_4$ is hydrogen, substituted alkyl (saturated or unsaturated) having from 1 to about 4 carbon atoms, or acyl.

30 Claims, No Drawings

PROCESS FOR MAKING GEMINAL BISPHOSPHONATES

CROSS REFERENCE

This application claims priority under Title 35, United States Code 119(e) from Provisional Application Ser. No. 60/179,506, filed Feb. 1, 2000.

TECHNICAL FIELD

The present invention relates to a novel process for making geminal bisphosphonates. The process provides for bisphosphorylation using phosphorus trihalide, molten phosphorous acid as a reactant/solvent, and a base as an acid acceptor/solvent.

BACKGROUND OF THE INVENTION

Polyphosphonic acids and their pharmaceutically-acceptable salts have been proposed for use in the treatment of diseases of bone and calcium metabolism. Such diseases include osteoporosis, hyperparathyroidism, hypercalcemia of malignancy, ostolytic bone metastases, myosistis ossificans progressiva, calcinoisis universalis, arthritis, neuritis, bursitis, tendonitis and other inflammatory conditions. In particular bisphosphonates, like ethane-1-hydroxy-1,1-diphosphonic acid (EHDP), propane-3-amimo-1-hydroxy-1,1-diphosphonic acid (APD), dichloromethane diphosphonic acid (C12MDP), 3-amino-1-hydroxy-propylidene-diphosphonic acid. (PAMIDRONATE), 4-amino-1-hydroxybutylidene-1,1-bisphosphonic acid (ALENDRONATE) and 1-hydroxy-2-(3-pyridinyl) ethylidene-1,1-bisphosphonic acid (RISEDRONATE) have been the subject of considerable research efforts in this area. Paget's disease and heterotropic ossification are currently successfully treated with EHDP. The diphosphonates tend to inhibit the resorption of bone tissue, which is beneficial to patients suffering from excessive bone loss. However, in spite of certain analogies in activity, bisphosphonates do not exhibit the same degree of activity and some have serious drawbacks with respect to the degree of toxicity in animals and the tolerability or the negative side effects in humans.

Several methods for making bisphosphonates have been disclosed. For example, European Patent Application 0 494 644, Instituto Gentili and PCT application WO96/33199 disclose methods for making amino-bisphosphonates. However, just as there are differences in the activities of the different bisphosphonates, so too are there differences in the method of making these compounds. Depending on the reaction conditions, the viscosity of the reaction mixture and/or the formation of large amounts of elemental phosphorus by-products limit the scale on which the bisphosphorylation reaction can be readily carried out.

It is therefore desirable to use a scaleable process to produce geminal bisphosphonates that achieves high yields with little residual elemental phosphorous by-products and that can be safely practiced on the commercial scale.

SUMMARY OF THE INVENTION

The present invention is directed to a process for making geminal bisphosphonates of the general formula:

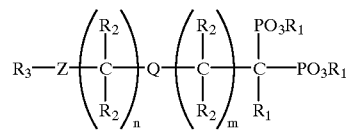

wherein Q is oxygen, $-NR_4-$, sulfur, selenium, or a single bond; m+n is an integer from 0 to about 5, Z is a ring selected from the group consisting of pyridine, pyridazine, pyrimidine, and pyrazine; $R_1$ is independently hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl; each $R_2$ is independently, hydrogen, or substituted or unsubstituted alkyl (saturated or unsaturated) having from 1 to about 4 carbon atoms; $R_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; $R_4$ is hydrogen, substituted alkyl (saturated or unsaturated) having from 1 to about 4 carbon atoms, or acyl; resulting from bisphosphorylation of an aminocarboxylic acid in the presence of phosphorus trihalide, molten phosphorous acid and base such as morpholine to form a geminal bisphosphonate.

DETAILED DESCRIPTION OF THE PRESENT INVENTION

The present invention is directed to a novel process for making geminal bisphosphonates. Said process involves the use of molten phosphorous acid, an amino carboxylic acid, phosphorous trihalide, and base in the bisphosphorylation step. The reaction is carried out at a temperature of from about 45° C. to about 90° C., preferably from about 55° C. to about 85° C., more preferably from about 60° C. to about 75° C. The presence of an additional solvent is optional. Particularly preferred geminal bisphosphonates made by this process are 1-hydroxy-2-(3-pyridinyl)ethylidine bisphosphonic acid, 4-amino-1-hydroxybutylidene-1,1-bisphonic acid, and 3-amino-1-hydroxypropylidene-diphosphonic acid. Most preferred is risedronate, 1-hydroxy-2-(3-pyridinyl)ethylidene-1,1-bisphosphonicacid.

Definitions and Usage of Terms

The following is a list of definitions for terms used herein:

As used herein, "alendronate" denotes 4-amino-1-hydroxybutylidene-1,1-bisphonic acid.

As used herein, "alkenyl" means a hydrocarbon substituent with one or more double bonds, straight or branched chain, unsubstituted or substituted.

As used herein, "alkoxy" means a substituent having the structure Q-O-, where Q is alkyl or alkenyl.

As used herein, "alkyl" means a saturated hydrocarbon substituent, straight or branched chain, unsubstituted or substituted.

As used herein, "alkylthio" means a substituent having the structure Q-S-, where Q is alkyl or alkenyl.

As used herein, "aminocarboxylic acid" is a saturated or unsaturated substituted or unsubstituted alkyl with a carboxylic acid group attached to one end and an amine group either attached to one of the carbons of the alkyl chain or as a heteroatom in a saturated or unsaturated substituted or unsubstituted heterocyclic ring.

As used herein, "base" means a basic reagent which is added to a reaction mixture to facilitate bisphosphorylation. Bases include organic and inorganic bases. Preferred bases include those which have easily filterable or otherwise removable salts. Specifically, preferred bases include N,N-diisopropylethylamine, triethylamine, trimethylamine, 4-dimethylaminopyridine, pyridine, potassium carbonate, sodium carbonate, potassium bicarbonate, sodium bicarbonate and morpholine. The more preferred bases are triethylamine, trimethylamine, potassium carbonate, pyridine and morpholine. The most preferred base is morpholine. The base may be added as the free base or in its salt form.

As used herein, "biohydrolyzable ester" is an ester moiety that does not interfere with the therapeutic activity of the compound, or that is readily metabolized by a human or other mammal.

As used herein, "bisphosphorylation" is the chemical reaction resulting in the production of a product containing two phosphoryl groups on the same carbon.

As used herein, "carbocyclic ring" is a saturated, unsaturated, or aromatic, hydrocarbon ring radical. Carbocyclic rings are monocyclic or are fused, bridged, or spiro polycyclic ring systems. Monocyclic rings contain from 3 to 9 atoms, preferably 4 to 7 atoms, and most preferably 5 or 6 atoms. Polycyclic rings contain from 7 to 17 atoms, preferably from 7 to 14 atoms, and most preferably 9 or 10 atoms.

As used herein, "halogen" is a chloro, bromo, fluoro, or iodo atom radical. Bromo and chloro are the most preferred halogens.

As used herein, "heterocyclic ring" is a saturated, unsaturated, or aromatic, ring radical comprised of carbon atoms and one or more heteroatoms in the ring. Heterocyclic rings are monocyclic or are fused, bridged, or spiro polycyclic ring systems. Monocyclic rings contain from 3 to 9 atoms, preferably 4 to 7 atoms, and most preferably 5 or 6 atoms. Polycyclic rings contain from 7 to 17 atoms, preferably from 7 to 14 atoms, and most preferably 9 or 10 atoms.

As used herein, "inorganic acid" is a mineral acid such as sulfuric, nitric, hydrochloric, phosphoric, and phosphorous.

As used herein, "methylene" is a —$CH_2$— radical.

As used herein, "molten phosphorous acid" means phosphorous acid heated to from about 45° C. to 95° C., preferably from about 55° C. to about 85° C., more preferably from about 60° C. to about 75° C.

As used herein, "organic acid" is an organic carboxylic acid, such as formic acid, acetic acid, chloroacetic acid, dichloroacetic acid, propionic acid, benzoic acid, maleic acid, fumaric acid, succinic acid, tartaric acid, and methane sulfonic acid.

As used herein, "phosphorus trihalide" is a tri-halogen substituted phosphorus. The more preferred phosphorus trihalide is phosphorus oxychloride, phosphorus oxybromide, phosphorus tribromide or phosphorus trichloride. Most preferred is phosphorus trichloride.

As used herein, "Pamidronate" denotes 3-amino-1-hydroxypropylidene-diphosphonic acid.

The term "risedronate", as used herein, denotes and 1-hydroxy-2-(3-pyridinyl)ethylidene-1,1-bisphosphonicacid and has the following structure:

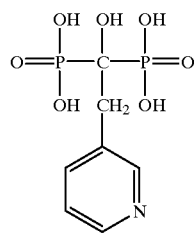

The compound risedronate is further described in U.S. Pat. No. 5,583,122, Benedict et al., assigned to the Procter & Gamble Co., issued Dec. 10, 1996, and "An American Conference, Bisphosphonates: Current Status and future Prospects," The Royal College of Physicians, London, England, May 21–22, 1990, organized by IBC Technical Services, both references hereby are incorporated by reference.

The term "bisphosphonate active ingredient" includes the bisphosphonate free acid, bisphosphonate salts, and bisphosphonate esters, or any mixture thereof. Any pharmaceutically-acceptable, non-toxic salt or ester of bisphosphonate may be used as the risedronate active ingredient in the novel oral dosage forms of the present invention. The salts of bisphosphonate may be acid addition salts, in particular the hydrochloride, but any pharmaceutically-acceptable, non-toxic organic or inorganic acid salt may be used. In addition, salts formed with the phosphonic acid group may be used, including, but not limited to alkali metal salts (K, Na) and alkaline earth metal salts (Ca, Mg) the Ca and Na salts being preferred.

Particularly, other esters of bisphosphonate which are suitable for use as the active ingredient herein are straight chain or branched chain $C_1$–$C_{18}$ alkyl esters, including, but not limited to, methyl, ethyl, propyl, isopropyl, butyl, isobutyl, amyl, hexyl, heptyl, octyl, nonyl, decyl, lauryl, myristyl, cetyl, and stearyl; straight chain or branched $C_2$–$C_{18}$ alkenyl, esters, including but not limited to vinyl, alkyl, undecenyl, and linolenyl; $C_3$–$C_8$ cycloalkyl esters, including, but not limited to, cyclopropyl, cyclobutyl, cyclopentyl, cyclohexyl, cycloheptyl, and cyclooctyl; aryl ester, including, but not limited to phenyl, toluyl, xylyl, and naphthyl; alicyclic esters, including, but not limited to, menthyl; and arylalkyl esters, including, but not limited to benzyl, and phenethyl.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, amino, aminoalkyl (e.g. aminomethyl, etc.), cyano, halogen, alkoxy, alkoxyacyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "solvent", is a substance capable of dissolving another substance to form a uniform solution. The solvent may either be polar or non-polar. Solvents for the bisphosphorylation reaction include but are not limited to inorganic acids, organic acids, and organic bases.

The Process

The bisphosphorylation step of the present process invention is conducted such that the corresponding aminocarboxylic acid is dissolved in molten phosphorous acid and reacted with phosphorus trihalide in the presence of a base, where the base is preferably morpholine or pyridine. The reaction is carried out in the temperature range between about 45° C. to about 90° C., preferably between about 55° C. to about 90° C., more preferably between about 55° C. to about 85° C., and most preferably between about 60° C. to about 75° C. The process described herein is readily adapted to industrial production.

Without a solvent, such as excess phosphorous acid, and a base the reaction mixture would be very viscous. The phosphorous acid and bases added in the process act as a solvent to give a uniform reaction mixture or solution. The amount of phosphorus trihalide added in relation to the aminocarboxylic acid is from about 1.7 equivalent to about 2.5 equivalents, preferably about 2 equivalents. The amount of phosphorous acid and phosphorus trihalide should be controlled to avoid the formation of pyrophoric elemental phosphorus. Phosphorus trichloride reacts with phosphorous acid under the reaction conditions consuming some of the phosphorus trichloride and liberating hydrochloric acid gas. Generally, the amount of phosphorous acid added in relation to the amiocarboxylic acid is from about 1.5 to about 6 equivalents, preferably from about 2 to about 6 equivalents, more preferably from about 2 to about 5.5 equivalents, most preferably 5 equivalents. The base is added in an amount appropriate to achieve the desired viscosity. The amount of base added in relation to the phosphorous acid is from about 0.2 to 0.8 equivalents, more preferably from about 0.4 to about 0.6 equivalents. The process described herein is readily adapted to industrial production.

This process is illustrated by the following general scheme:

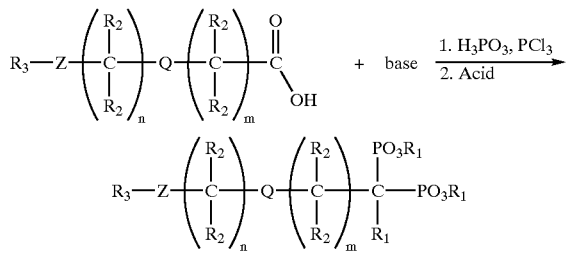

wherein Q is oxygen, —NR4—, sulfur, selenium, or a single bond; m+n is an integer from 0 to about 5, Z is a ring selected from the group consisting of pyridine, pyridazine, pyrimidine, and pyrazine; R1 is independently hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl,; each R2 is independently, hydrogen, or substituted or unsubstituted alkyl (saturated or unsaturated) having from 1 to about 4 carbon atoms; R3 is one or more substituents selected from the group consisting of hydrogen, substituted or unsubstituted alkyl (saturated or unsaturated) having from 1 to about 6 carbon atoms, substituted and unsubstituted arly, substituted and unsubstituted benzyl, hydroxy, halogen, carbonyl, alkoxy, nitro, amido, amino, substituted amino, carboxylate, and combinations thereof; R4 is hydrogen, substituted alkyl (saturated or unsaturated) having from 1 to about 4 carbon atoms, or acyl; resulting from bisphosphorylation of an aminocarboxylic acid in the presence of phosphorus trihalide, molten phosphorous acid and base such as morpholine to form a geminal bisphosphonate.

The following non-limiting examples illustrate the processes of the present invention.

EXAMPLE 1

Bisphosphorylation of 3-PAA HCl to give 1-Hydroxy-2-(3-pyridinyl)ethylidene-1,1-bisphosphonic acid

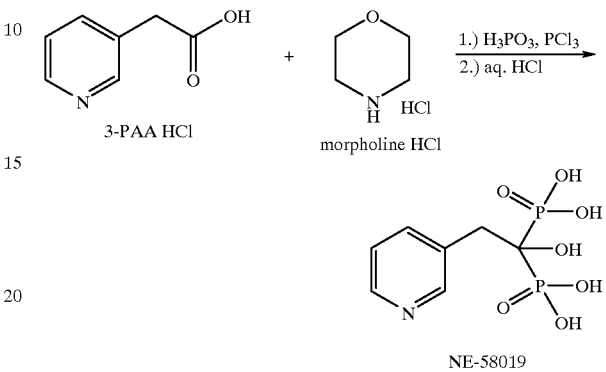

1-Hydroxy-2-(3-pyridinyl)ethylidene-1,1-bisphosphonic acid

The reaction is run on the 65 mol scale in a 30 gal reactor. The mixture of 5 eq phosphorous acid and 3-PAA.HCl, with morpholine.HCl, is melted together until complete solution is obtained at about 70–75° C. The reaction mixture is cooled to 68° C. and 2 eq of $PCl_3$ is metered in over 2.5–4 hours while maintaining the temperature at 68° C. The reaction is allowed to continue 15–30 min. after the addition is complete. Then the reaction mixture is hydrolyzed in aqueous hydrochloric acid at 80° C. for 0.5 hr to yield, after crystallization from aqueous acid/IPA, 14.2 Kg of NE-58019 in a 77.6% isolated yield.

EXAMPLE 2

Bisphosphorylation of 3-PAA HCl to give 1-Hydroxy-2-(3-pyridinyl)ethylidene-1,1-bisphosphonic acid

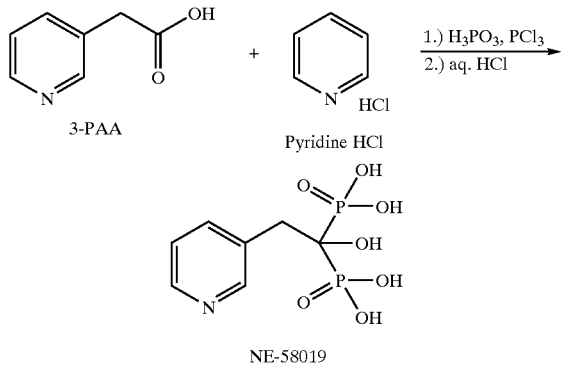

The mixture of 5 eq. phosphorous acid, 1.5 eq. pyridine-.HCl and 3-PAA is melted together until a uniform melt is formed (80–90° C.). Then 2.1 eq. of pyridine are added. The reaction is cooled to about 70° C. and 2 eq. of $PCl_3$ are slowly added. The mixture is heated at about 70° C. for 3.5 hours. Water and HCl are added, the reaction hydrolyzed for about 30 to about 45 minutes at 75° C. to yield risedronate after crystallization from aqueous acid/IPA.

EXAMPLE 3

Bisphosphorylation of B-alanine to give pamidronate

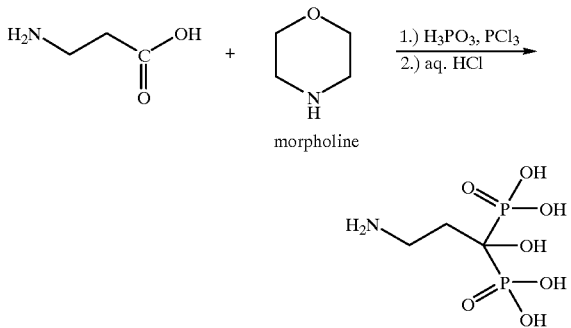

The mixture of 5 eq. phosphorous acid and β-alanine is heated to form a melt. Morpholine (1 eq.) is slowly added. The reaction is cooled to about 70° C. and 2 eq. of $PCl_3$ are added. The mixture is heated for about 3.5 hours. Then the reaction is hydrolyzed in aqueous acid at about 75° C. for about 0.5 hours. Crystallization from aqueous acid/IPA, affords pamidronate.

EXAMPLE 4

Bisphosphorylation of 4-amino butyric acid to form 4-amino-1-hydroxybutylidene-1,1-bisphosphonic acid

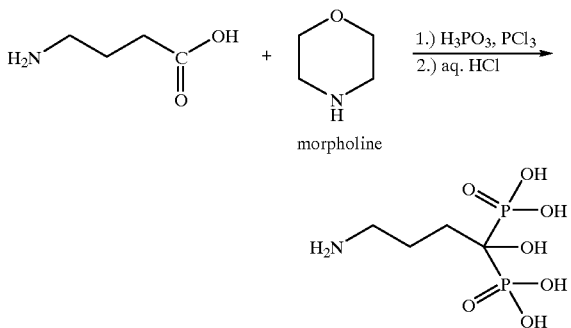

The mixture of 5 eq. phosphorous acid, 4-aminobutyric acid and morpholine. HCl is melted together until uniform solution is formed. The reaction mixture is cooled to about 70° C. and 2 eq. of $PCl_3$ are carefully added. The mixture is heated for about 5.5 hours before the reaction mixture is hydrolyzed in aqueous acid at about 80° C. and alendronate is isolated from an ethanolic solution.

Compositions

The compounds made herein may be used in pharmaceutical compositions. The term "pharmaceutical composition" means a dosage form comprised of a safe and effective amount of an active ingredient and pharmaceutically-acceptable excipients. The pharmaceutical compositions described herein are comprised of from about, 0.1% to about 99%, preferably from about 0.5% to about 95% of an active ingredient, and from about 1% to about 99.9%, preferably from 5.00% to about 99.90% of pharmaceutically-acceptable excipients. For risedronate the composition comprises, preferably 0.25% to 40%, preferably from about 0.5% to about 30% of a risedronate active ingredient and from about 60% to about 97%, preferably from about 70% to about 99.5% of pharmaceutically-acceptable excipients.

The phrase "safe and effective amount", as used herein means an amount of a compound or composition high enough to significantly positively modify the symptoms and/or condition to be treated, but low enough to avoid serious side effects (at a reasonable benefit/risk ratio), within the scope of sound medical judgment. The safe and effective amount of active ingredient for use in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular active ingredient selected for use. Pharmaceutically-acceptable excipients include, but are not limited to, polymers, resins, plasticizers, fillers, lubricants, binders, disintegrants, solvents, co-solvents, buffer systems, surfactants, preservatives, sweetening agents, flavoring agents, pharmaceutical grade dyes and pigments. All or part of the pharmaceutically-acceptable excipients contained in the pharmaceutical compositions described herein is used to make the film coating which is to be utilized in the novel oral dosage forms described herein.

The term "oral dosage form" as used herein means any pharmaceutical composition intended to be administered to the stomach of an individual via the mouth of said individual, and for purposes of the present invention, the preferred delivery form is in the form of a modified oval tablet (preferably film coated) containing granules or particles of active ingredient.

As stated hereinabove, pharmaceutically-acceptable excipients include, but are not limited to polymers, resins, plasticizers, fillers, lubricants, binders, disintegrants, solvents, co-solvents, surfactants, preservatives, sweetener agents, flavoring agents, buffer systems, pharmaceutical-grade dyes and pigments.

The preferred solvent for the pharmaceutical composition is water.

Flavoring agents among those useful herein include those described in *Remington's Pharmaceutical Sciences,* 18th Edition, Mack Publishing Company, 1990, pp. 1288–1300, incorporated by reference herein. Dyes, or pigments among those useful herein include those described in *Handbook of Pharmaceutical Excipients,* Second Edition pp. 126–134, 1994 by the American Pharmaceutical Association & the Pharmaceutical Press, incorporated by reference herein.

Preferred co-solvents include, but are not limited to, ethanol, glycerin, propylene glycol, polyethylene glycol.

Preferred buffer systems include, but are not limited to potassium acetate, boric carbonic, phosphoric, succinic, malic, tartaric, citric, acetic, benzoic, lactic, glyceric, gluconic, glutaric and glutamic. Particularly preferred are phosphoric, tartaric, citric, and potassium acetate.

Preferred surfactants include, but are not limited to, polyoxyethylene sorbitan fatty acid esters, polyoxyethylene monoalkyl ethers, sucrose monoesters and lanolin esters and ethers.

Preferred preservatives include, but are not limited to, phenol, alkyl esters of parahydroxybenzoic acid, benzoic acid and the salts thereof, boric acid and the thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben.

Preferred sweeteners include, but are not limited to, sucrose, glucose, saccharin, and aspartame. Particularly preferred are sucrose and saccharin.

Preferred binders include, but are not limited to methycellulose, sodium carboxymethycellulose, hydroxypropylmethylcellulose, carbomer, povidone, acacia, guar gum, xanthan gum and tragacanth. Particularly preferred are methycellulose, carbomer, xanthan gum, guar gum, povidone and sodium carboxymethycellulose.

Preferred fillers include, but are not limited to lactose, sucrose, maltodextrin, mannitol, starch, and microcrystalline cellulose.

Preferred plasticizers include, but are not limited to polyethylene glycol, propylene glycol, dibutyl phthalate, and castor oil, acetylated monoglycerides, and triacetin.

Preferred lubricants include, but are not limited to, magnesium stearate, stearic acid, and talc.

Preferred disintegrants include, but are not limited to, crospovidone, sodium carboxymethyl starch, sodium starch glycolate, sodium carboxymethyl cellulose, alginic acid, clays, and ion exchange resins.

Preferred polymers, include but are not limited to hydroxypropylmethylcellulose (HPMC) alone and/or in combination with hydroxypropylcellulose (HPC), carboxymethylcellulose, acrylic resins such as Eudragit® RL30D, manufactured by Rohm Pharma GmbH Weiderstadt, West Germany, methylcellulose, ethylcellulose, and polyvinylpyrrolidone or other commercially available film-coating preparations such as Dri-Klear, manufactured by Crompton & Knowles Corp., Mahwah, N.J. or Opadry manufactured by Colorcon, West Point, Pa.

The bisphosphonates of the present invention are generally more biologically potent in inhibiting bone resorption. Thus, the compositions of the present invention allow for greater flexibility in dosage administration and dosing intervals. For example, the compositions of the present invention, including oral compositions, may be dosed, daily, weekly, biweekly or monthly.

What is claimed is:

1. A process for making a geminal bisphosphonate of the formula:

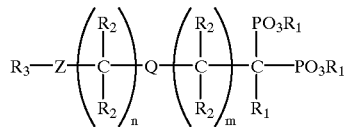

wherein Q is oxygen, —NR4—, sulfur, selenium, or a single bond; m+n is an integer from 0 to about 5, Z is a ring selected from the group consisting of pyridine, pyridazine, pyrimidine, and pyrazine; $R_1$ is hydroxy; each $R_2$ is independently, hydrogen, or substituted or unsubstituted alkyl (saturated or unsaturated) having from 1 to about 4 carbon atoms; $R_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof; $R_4$ is hydrogen, substituted alkyl (saturated or unsaturated) having from 1 to about 4 carbon atoms, or acyl; comprising the steps of:
   a) providing an aminocarboxylic acid;
   b) dissolving the aminocarboxylic acid in phosphorous acid; and
   c) reacting the solution of step b) with phosphorus trihalide in the presence of base.

2. The process of claim 1 wherein the base is selected from the group comprising N,N-diisopropylethylamine, triethylamine, trimethylamine, 4-dimethylaminopyridine, pyridine, potassium carbonate, sodium carbonate, potassium bicarbonate, sodium bicarbonate, and morpholine.

3. The process of claim 2 wherein the phosphorous acid is heated from about 45° C. to about 95° C. until molten.

4. The process of claim 3 wherein the phosphorus trihalide is selected from the group comprising phosphorus oxychloride, phosphorus oxybromide, phosphorus tribromide and phosphorus trichloride.

5. The process of claim 4 wherein the base is selected from the group comprising morpholine, triethylamine, trimethylamine, pyridine and potassium carbonate.

6. The process of claim 5 wherein the phosphorous acid is heated from about 55° C. to about 85° C. until molten.

7. The process of claim 6 wherein the phosphorus trihalide is phosphorus trichloride.

8. The process of claim 7 wherein the geminal bisphosphonate is 1-hydroxy-2-(3-pyridinyl)ethylene bisphosphonic acid.

9. The process of claim 8 wherein the base is morpholine.

10. The process of claim 9 wherein the ratio of phosphorus trihalide to aminocarboxylic acid is from about 1.7 to about 3 equivalents.

11. The process of claim 10 wherein the ratio of phosphorous acid to aminocarboxylic acid is from about 1.5 to about 6 equivalents.

12. The process of claim 11 wherein the ratio of base to phosphorous acid is from about 0.2 to about 0.8 equivalents.

13. The process of claim 12 wherein the geminal bisphosphonate is risedronate.

14. The process of claim 13 wherein the ratio of phosphorus trihalide to amino carboxylic acid is about 2 equivalents.

15. The process of claim 14 wherein the ratio of phosphorous acid to aminocarboxylic acid is about 5 equivalents.

16. The process of claim 15 wherein the ratio of base to phosphorous acid is from about 0.4 to about 0.6 equivalents.

17. A process for making a geminal bisphosphonate having the formula:

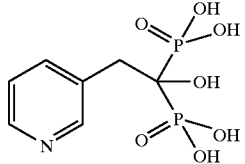

said process comprising the steps of:
   a) mixing 3-pyridylacetic acid, a base, and phosphoric acid together at a temperature of from about 45° C. to about 90° C. to form a 3-pyridylacetic acid containing admixture; and b) reacting said admixture with a phosphorous trihalide to form 1-hydroxy-2-(3-pyrindinyl)ethylidene-1,1-bisphosphonate.

18. The process of claim 17 further comprising the step of:
c) adding water and HCl to hydrolyze any unreacted starting material.

19. The process of claim 15 further comprising the step of:
d) isolating the 1-hydroxy-2-(3-pyrindinyl)ethylidene-1,1-bisphosphonate obtained in step (b) from the hydrolyzed unreacted starting material.

20. The process of claim 19 further comprising the step of:
e) crystallizing the 1-hydroxy-2-(3-pyrindinyl)ethylidene-1,1-bisphosphonate obtained in step (d) from aqueous acid/isopropyl alcohol.

21. The process of claim 17 wherein the ratio of phosphorous trihalide to 3-pyridylacetic acid is from about 1.5 equivalents to about 6 equivalents.

22. The process of claim 21 wherein the ratio of phosphorous trihalide to 3-pyridylacetic acid is from about 1.7 equivalents to about 3 equivalents.

23. The process of claim 17 wherein the ratio of base to phosphorous acid is from about 0.2 equivalents to about 0.8 equivalents.

24. The process of claim 17 wherein said base is selected from the group comprising N,N-diisopropylethylamine, triethylamine, trimethylamine, 4-dimethylaminopyridine, pyridine, potassium carbonate, sodium carbonate, potassium bicarbonate, sodium bicarbonate, or morpholine.

25. The process of claim 24 wherein said base is selected from the group comprising morpholine, triethylamine, trimethylamine, pyridine or potassium carbonate.

26. The process of claim 25 wherein said base in morpholine.

27. The process of claim 17 wherein said phosphorus trihalide is selected from the group comprising phosphorus oxychloride, phosphorus oxybromide, phosphorus tribromide or phosphorus trichloride.

28. The process of claim 27 wherein the phosphorous trihalide is phosphorous trichloride.

29. The process of claim 17 wherein step (a) is conducted at a temperature of about 55° C. to about 85° C.

30. A process for making a geminal bisphosphonate having the formula:

said process comprising the steps of:
a) mixing 3-pyridylacetic acid, morpholine hydrochloride, and phosphoric acid together at a temperature of from about 70° C. to about 75° C. to form a 3-pyridylacetic acid containing admixture;
b) cooling said admixture to 68° C.; and
c) reacting said admixture with a phosphorous trihalide to form 1-hydroxy-2-(3-pyrindinyl)ethylidene-1,1-bisphosphonate.

* * * * *

UNITED STATES PATENT AND TRADEMARK OFFICE
CERTIFICATE OF CORRECTION

PATENT NO.    : 6,562,974 B2
DATED         : May 13, 2003
INVENTOR(S)   : Frederick Dana Cazer et al.

It is certified that error appears in the above-identified patent and that said Letters Patent is hereby corrected as shown below:

Column 1,
Line 31, delete "1" and insert -- l -- the formula (C12MDP).

Column 6,
Line 61, delete "." and insert -- • -- before "HCl".

Column 7,
Line 50, delete "." and insert -- • -- before "HCl".

Column 11,
Line 7, delete "15" and insert -- 18 --.

Signed and Sealed this

Ninth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,562,974 B2 Page 1 of 1
DATED : May 13, 2003
INVENTOR(S) : Frederick Dana Cazer et al.

It is certified that error appears in the above-identified patent and that said Letters Patent is hereby corrected as shown below:

Column 10,
Line 64, delete "phosphoric" and insert -- phosphorous --.

Column 12,
Line 23, delete "phosphoric" and insert -- phosphorous --.

Signed and Sealed this

Sixth Day of September, 2005

JON W. DUDAS
*Director of the United States Patent and Trademark Office*